United States Patent [19]

Kerry et al.

[11] 4,239,774
[45] Dec. 16, 1980

[54] PESTICIDAL COMPOSITIONS CONTAINNG 1,3,5-TRIAZAPENTA-1,4-DIENE AND ORGANO-TIN OXIDE COMPOUNDS

[75] Inventors: John C. Kerry; David M. Weighton, both of Nottingham, England

[73] Assignee: The Boots Company Limited, Nottingham, England

[21] Appl. No.: 94,838

[22] Filed: Nov. 16, 1979

Related U.S. Application Data

[63] Continuation of Ser. No. 920,156, Jun. 29, 1978, abandoned.

[30] Foreign Application Priority Data

Jul. 1, 1977 [GB] United Kingdom ............... 27539/77

[51] Int. Cl.³ ...................... A01N 55/04; A01N 37/52
[52] U.S. Cl. ...................................... 424/288; 424/326
[58] Field of Search ................. 424/288, 330; 424/326

[56] References Cited

U.S. PATENT DOCUMENTS 3,264,177  8/1966  Kenaga ................................ 424/288
3,657,451  4/1972  Horne, Jr. ........................... 424/288

FOREIGN PATENT DOCUMENTS 1327935  8/1973  United Kingdom .................... 424/330

Primary Examiner—Douglas W. Robinson
Attorney, Agent, or Firm—Gordon W. Hueschen

[57] ABSTRACT

Pesticidal compositions containing amitraz and a pesticidal tin compound selected from cyhexatin and fenbutatin oxide, are described. The compositions, which preferably comprise the active ingredients in the ratio of 1:10 to 10:1 by weight, are synergistic and have activity against a wide range of insect and acarid pests. They are particularly useful in controlling pests on fruit crops.

8 Claims, No Drawings

PESTICIDAL COMPOSITIONS CONTAINNG 1,3,5-TRIAZAPENTA-1,4-DIENE AND ORGANO-TIN OXIDE COMPOUNDS

This is a continuation of application Ser. No. 920,156, filed June 29, 1978 now abandoned.

This invention relates to a pesticidal composition and methods of controlling pests.

A problem constantly facing farmers with the need to control pests attacking crops is the build up of resistance to pesticides. There is always a need for improved materials which are not only more effective against particular pests but are also versatile and can be used to combat a wide spectrum of pests.

We have now discovered that mixtures of the pesticide, amitraz, with certain pesticidal tin compounds, have valuable and unexpected properties. For example in the context of certain pests which attack crops we have observed that the pesticidal activity of the mixtures is greater than would be expected from merely combining them together and synergism is exhibited.

Accordingly the invention provides a pesticidal composition comprising amitraz and a pesticidal tin compound selected from the group consisting of cyhexatin and fenbutatin oxide, the components being present in a ratio of between 1:10 to 10:1 by weight and especially between 1:5 to 5:1 by weight.

Amitraz has the chemical formula 1,5-di-(2,4-dimethylphenyl)-3-methyl-1,3,5-triazapenta-1,4-diene and cyhexatin is tricyclohexyltin hydroxide available, for example, under the trade name Plictran. Fenbutatin oxide is di[tri-(2-methyl-2-phenylpropyl)tin]oxide available, for example, as Torque.

Preferred embodiments of the invention are pesticidal compositions comprising (a) amitraz and cyhexatin and (b) amitraz and fenbutatin oxide. Naturally it is also possible to obtain the advantages of the invention by using a composition comprising both of the pesticidal tin compounds in admixture with amitraz or by the addition of other pesticides which do not affect the interaction between amitraz and the pesticidal tin compound.

In addition to the synergistic activity referred to above, the mixtures of the invention are active against a wide range of pests, both insects and acarids, and one of their advantages stems from the fact that they can be applied to a crop attacked by pests at all stages of their life cycle. This is an important advantage since the timing of pesticide application is made less critical and there is a greater chance of obtaining good, overall, control of the pests in a single treatment. Amongst the pests which can be controlled are insects such as aphids for example the green peach aphid *Myzus persicae*: codling moth *Cydia pomenella*; cabbage white butterfly *Pieris brassicae*; pear psylla *Psylla pyri*; and scale insects such as Califormia red scale *Acnidiella annantii*; and acardis (pests of the order Acarina) such as for example the spider mites *Tetranychus urticae, Tetranychus citri, Panonychus ulmi* and Panonychus citri. These pests attack important crops and in doing so cause great economic damage. Thus the mixtures find application on cotton, maize and soybean crops, on soft fruit and particularly on top fruit such as apple, pear, peach and citrus crops.

When employing a composition comprising amitraz and cyhexatin the two components are preferably in the ratio of between 1:4 and 4:1, especially between 1:2 and 2:1 by weight. In compositions comprising amitraz and fenbutatin oxide, the ratio is preferably between 1:4 and 4:1, especially between 1:2 and 2:1 by weight.

The compositions of the invention can be employed in a wide variety of forms and can comprise a liquid or solid diluent optionally together with a surface active agent. They are often most conveniently prepared in aqueous form immediately prior to use, for example, as a spray for pestinfested crops. One such method is commonly called "tank mixing" in which the two, or more, pesticide ingredients in their commercially available forms are mixed together by the farmer in a quantity of water for direct application. The concentration of the active ingredients for application to a crop by conventional ground methods is preferably within the range of from 0.001 to 10 percent, especially from 0.005 to 5 percent by weight of the composition, but more concentrated compositions containing up to 20 percent by weight may be desirable in the case of aerial sprays.

The compositions of the invention include not only those in suitable form for direct application but also concentrated primary compositions which can be supplied to the user and which require dilution with a suitable quantity of water or other diluent before application. Such compositions may comprise a surface active agent in addition to the active ingredients and typical examples are an aqueous dispersion, an aqueous emulsion, an emulsifiable concentrate, a dispersible powder or a dusting powder. As a concentrated primary composition the concentration of active ingredients can vary widely and can be for example from 5 o 95 percent by weight of the composition.

An emulsifiable concentrate, also known as a "miscible liquid", comprises a solution of the active ingredients in a water-immiscible solvent in association with one or more emulsifying agents. An emulsion is formed when the emulsifiable concentrate is mixed with water.

A dispersible powder comprises the active ingredients in finely divided form in association with one or more dispersing agents so that a stable aqueous dispersion of the active ingredients is formed on mixing the powder with water. A finely divided inert solid diluent such as kaolin or celite is generally incorporated in the dispersible powder.

A dusting powder comprises the active ingredients intimately mixed with a solid pulverulent diluent, for example kaolin.

As a further aspect, the invention includes a method for controlling pests which comprises applying a composition comprising amitraz and a pesticidal tin compound to the locus of the pests, that is, the pests or their habitat. More particularly the invention comprises a method for protecting plants from insects and acarids by the use of such compositions and especially by employing composition (a) or (b) described above, applied most conveniently as a foliar spray at a rate, for example, of from 0.25 to 6.0 kilograms per hectare.

A wide variety of crops including cotton, maize, soybeans and fruit crops can be protected by treatment with the pesticidal composition of the invention, but the method of the invention finds particular application to fruit crops such as vines, soft fruit such as for example raspberries, gooseberries, strawberries and red currants and top fruit such as for example apple, pear, peach and citrus crops. Thus the invention includes a method for controlling acarid and insect pests on a fruit crop which comprises applying a composition of the invention to the crop infested with pests. Some pests such as psyllid pests, codling moths and spider mites are especially serious on top fruit such as apple, pear and peach crops and thus an aspect of the invention is the control of such pests on top fruit, particularly by the application of compositions (a) or (b) referred to above. Application rates of the active ingredients preferably fall within the range of from 0.25 to 6.0 kilograms per hectare, for example from 0.5 to 2.5 kilograms per hectare. More than one application of pesticide may often be desirable and, when fruit crops are concerned, treatment at intervals of 3 to 30 days is often suitable.

The invention is illustrated by the following Examples.

EXAMPLES 1 AND 2

1. The activity of pesticidal compositions against adults of Tetranychus urticae were tested according to the following procedure.

French bean leaf discs, 2 cm in diameter, were cut to retain the petiole which was kept in contact with water throughout the test. Fifteen adult mites of *Tetranychus urticae* were placed on a leaf disc, which was then sprayed to the point of run-off with an aqueous solution or dispersion of amitraz and cyhexatin, both separately and together as mixtures. Percentage mortality was recorded after 72 hours.

The activity of each active component was read from dose response curves and an expected value for the mixture calculated. A comparison of these values with the data observed demonstrates that the mixtures have a synergistic effect.

| Amitraz (ppm) | Activity mortality (%) | Cyhexatin (ppm) | Activity mortality (%) | Calculated effect of mixture (%) | Observed effect of mixture (%) |
|---|---|---|---|---|---|
| 225 | 58 | 100 | 30 | 88 | 100 |
| 150 | 44 | 200 | 50 | 94 | 99 |
| 112.5 | 39 | 50 | 9 | 48 | 93 |
| 75.0 | 36 | 100 | 30 | 66 | 86 |
| 37.5 | 22 | 150 | 41 | 63 | 79 |
| 37.5 | 22 | 20 | 0 | 22 | 67 |
| 25.0 | 13 | 50 | 9 | 22 | 63 |
| 12.5 | 0 | 50 | 9 | 9 | 53 |

2. A similar test to that described above in Example 1 was carried out for mixtures of amitraz and fenbutatin oxide. The activity of amitraz was again determined under the conditions of the new test. The data shows evidence of synergism in the mixtures of the invention.

| Amitraz (ppm) | Activity mortality (%) | Fenbutatin oxide (ppm) | Activity mortality (%) | Calculated effect of mixture (%) | Observed effect of mixture (%) |
|---|---|---|---|---|---|
| 240 | 43 | 60 | 24 | 67 | 75 |
| 150 | 38 | 150 | 42 | 80 | 90 |
| 120 | 27 | 30 | 5 | 32 | 98 |
| 75 | 15 | 75 | 29 | 44 | 79 |
| 60 | 10 | 240 | 60 | 70 | 92 |
| 40 | 2 | 10 | 0 | 2 | 14 |
| 30 | 0 | 120 | 40 | 40 | 64 |
| 25 | 0 | 25 | 0 | 0 | 35 |
| 10 | 0 | 40 | 14 | 14 | 38 |

What is claimed is:

1. An acaricidal composition comprising as essential active ingredients 1,5-di-(2,4-dimethylphenyl)-3-methyl-1,3,5-triazapenta-1,4-diene and an organo-tin compound selected from the group consisting of tricyclohexyltin hydroxide and di[tri-(2-methyl-2-phenylpropyl)tin]oxide, the essential active ingredients being present in a ratio of between 1:4 to 4:1 by weight.

2. A composition according to claim 1 in aqueous form suitable for direct application to a crop, in which the concentration of essential active ingredients is 0.005 to 5 percent by weight.

3. A method for combating acarids which comprises applying an acaricidally effective amount of a composition according to claim 1 to said acarids or their habitat.

4. A method for protecting a crop selected from the group consisting of cotton, maize, soybeans, soft fruit and top fruit, by applying to said crop an acaricidally effective amount of a composition according to claim 1.

5. A method according to claim 4 in which the essential active ingredients are applied at a rate of 0.5 to 6.0 kilograms per hectare.

6. A method according to claim 5 which comprises treating a fruit crop by foliar application.

7. An acaricidal composition comprising as essential active ingredients 1,5-di-(2,4-dimethylphenyl)-3-methyl-1,3,5-triazapenta-1,4-diene and tricyclohexyltin hydroxide in the ratio of 1:4 to 2.25:1 by weight, the said diene compound being present in a concentration of at least about 12.5 parts per million.

8. An acaricidal composition comprising as essential active ingredients 1,5-di-(2,4-dimethylphenyl)-3-methyl-1,3,5-triazapenta-1,4-diene and di[tri-(2-methyl-2-phenyl-propyl)tin]oxide in the ratio of 1:4 to 4:1 by weight, the said diene compound being present in a concentration of at least about 10 parts per million.

* * * * *

UNITED STATES PATENT AND TRADEMARK OFFICE
CERTIFICATE OF CORRECTION

PATENT NO. : 4,239,774

DATED : December 16, 1980

INVENTOR(S) : John C. Kerry and David M. Weighton

It is certified that error appears in the above-identified patent and that said Letters Patent are hereby corrected as shown below:

[54] Title; "CONTAINNG" should read -- CONTAINING -- (Notice of Allowance and Base Issue Fee Due)
Col. 1, line 1 of Title; "CONTAINNG" should read -- CONTAINING -- (Notice of Allowance and Base Issue Fee Due)
Col. 1, line 57; "Acnidiella" should read -- Aonidiella --
Col. 2, line 9; "pestinfested" should read -- pest-infested --
Col. 3, line 17; "Tetranychus urticae" should be italicized Signed and Sealed this Ninth Day of June 1981

[SEAL]

Attest:

RENE D. TEGTMEYER

*Attesting Officer*  *Acting Commissioner of Patents and Trademarks*